United States Patent [19]

Burnham

[11] 4,032,590

[45] June 28, 1977
::::

[54] OLIGOMERIZATION OF ETHYLENE

[75] Inventor: David Robert Burnham, Runcorn, England

[73] Assignee: Imperial Chemical Industries Limited, London, England

[22] Filed: Aug. 18, 1975

[21] Appl. No.: 605,506

[30] Foreign Application Priority Data

Aug. 29, 1974 United Kingdom ............ 37774/74

[52] U.S. Cl. ..................................... 260/683.15 D
[51] Int. Cl.$^2$ ......................................... C07C 3/10
[58] Field of Search ........................... 260/683.15 D

[56] References Cited

UNITED STATES PATENTS

| | | | |
|---|---|---|---|
| 3,652,687 | 3/1972 | Bergem et al. | 260/683.15 D |
| 3,697,617 | 10/1972 | Yoo et al. | 260/683.15 D |
| 3,725,306 | 4/1973 | Yoo | 260/683.15 D |
| 3,755,490 | 8/1973 | Yoo | 260/683.15 D |

Primary Examiner—C. Davis
Attorney, Agent, or Firm—Cushman, Darby & Cushman

[57] ABSTRACT

Ethylene is oligomerized to predominantly α-olefins, principally butene-1 with some hexene-1, by contacting it with a catalyst comprising the product of reacting a weak field ligand complex of a Group VIII metal with a particulate inorganic oxide possessing sufficient Bronsted acidity to displace one of the ligands from the complex, in the presence of a Group I to III metal hydrocarbyl. Nickel and cobalt are preferred metals, typical weak field ligands being acetylacetonate and carboxylate. Preferred inorganic oxide supports are aluminium and zirconium phosphates. Selectivities of >90% may be obtained.

12 Claims, No Drawings

OLIGOMERIZATION OF ETHYLENE

This invention relates to the oligomerisation of ethylene and, especially, to its oligomerisation to predominantly α-olefins.

Many catalysts have been proposed for the oligomerisation of ethylene, commonly involving Group VIII metal compounds in conjunction with metal alkyls, for example aluminium alkyls. When such catalysts are used homogeneously difficulty is often experienced in separating them from the oligomeric products. In order to alleviate this difficulty, it has further been proposed to support the Group VIII metal compounds and metal alkyls on particulate inorganic materials, for example silica, and then to use the resulting supported catalysts heterogeneously, thus greatly facilitating their separation from the products.

However, in both heterogeneous and homogeneous systems it has been common practice to add Lewis bases, most commonly organic phosphines, to the systems to make them more selective.

We have now found that certain Group VIII metal compounds, when supported on defined support materials, may be used for the heterogeneous catalysis of ethylene to predominatly α-olefins without the addition of Lewis bases, especially the toxic organic phosphines.

According to one aspect of the present invention, a process for the oligomerisation of ethylene comprises contacting the ethylene with a catalyst which is the reaction product of a weak field ligand complex of a metal of Group VIII of the Periodic Table and an inorganic oxide support material which possesses sufficient Bronsted acidity to displace at least one of the ligands attached to the said Group VIII metal, in the presence of a hydrocarbyl of a metal of groups I to III of the Periodic Table.

Preferred Group VIII metals are cobalt, nickel and palladium; but nickel and cobalt are especially preferred.

Within the phrase "weak field ligand complex" is included the β-diketones, β-ketocarboxylic acid esters and salts of saturated and unsaturated carboxylic acids. Examples of such complexes include nickel acetonylacetonate, nickel naphthenate, nickel acetate, nickel benzoate, and nickel 4-cyclohexyl butyrate.

In general the ligands are those which contain from 2 to 20 carbon atoms.

The precise nature of the ligands is not critical, provided that at least one of them may be displaced by reaction with the support material.

Preferred acidic inorganic oxide supports which may be used in our invention are finely divided oxides of aluminium, silicon and zirconium containing other elements which impart the necessary Bronsted acidity to the support material. Examples of said other elements include phosphorus and fluorine. These may be present in chemical combination with the oxide of the support material, for example, as zirconium, aluminium or calcium phosphate; or they may be added to the oxide support by a suitable pretreatment, for example by treating silica with phosphorus trichloride.

The ability of a potential support material to displace a ligand of the Group VIII metal compound may be established by simple experiment. For example, the dry support material may be slurried with a dry, oxygenfree hydrocarbon solvent, for example toluene, or hexane, and a solution of the Group VIII metal compound in a hydrocarbon solvent (preferably the same solvent as used for the slurry) then added to the slurry. The mixture is then stirred for about 1 hour and then allowed to settle. The supernatant liquid is then tested for the presence of the displaced ligand. This may be done visually where the liqand gives rise to a coloured solution in the solvent being used. Otherwise or additionally the presence of the ligan may be detected by any suitable analytical method, for example by gas liquid chromatography (GLC). In the above test, all operations are preferably conducted under an atmosphere of dry nitrogen.

The support preferably has a surface area $> 10$ $m^2/g$, and is dried to remove moisture before being treated with the Group VIII metal complex in a hydrocarbon solvent. A drying temperature of $>120°$ C may be used; but preferably the support is calcined at a higher temperature, for example $>200°$ C before use, especially when aluminium phosphate is used as a support. However, the precise drying temperature will depend on the actual support material used; but must not be so high as to remove all the surface hydroxyl groups from the support.

The concentration of the Group VIII metal complex on the support material can have any value up to saturation but for efficient use of support the concentration of metal complex is preferably $>0.01$ m moles/g, and especially at least 0.1 m moles/g.

Suitable hydrocarbyl compounds of metals of Groups I to III of the Periodic Table which may be used as cocatalysts in our process include the metal alkyls or metal alkyl halides of aluminium, magnesium or lithium. Especially suitable are the alkyls of aluminium, for example trimethyl, triethyl or tribenzyl aluminium. The molar ratio of hydrocarbyl co-catalyst to Group VIII metal compound may be most readily expressed as a Group I to III metal/Group VIII metal ratio. This ratio may be in the range 100 to 0.1; but is preferably in the range 20 to 1 or more preferably 10 to 1.

Catalysts suitable for use in our process may be prepared by contacting the chosen support material with a solution of the Group VIII metal compound in a hydrocarbon solvent, usually at ambient temperature, although temperatures in the range 0°–200° C may be used. It is preferred to first slurry the support in the solvent and then add the solution of Group VIII metal compound to the slurry, stirring the mixture to enable displacement of ligand to take place (typically 1 hour). The Group I to III metal hydrocarbyl compound may then be added to the slurried reaction product to form the final supported catalyst which is then contacted with ethylene. Alternatively, the ethylene may be contacted with the supported Group VIII metal compound and the Group I to III metal hydrocarbyl subsequently introduced to initiate the oligomerisation process.

Although it is not essential to remove the displaced ligand (e.g. acetylacetone) from the mixture after reaction, it is often convenient to allow the reacted slurry to settle and to remove the supernatant liquid, e.g. by decantation.

According to a second aspect of our invention, we provide a catalyst component useful for the oligomerisation of ethylene to predominantly α-olefins which comprises the product of reacting a weak-field ligand complex of a Group VIII metal with a particulate inorganic oxide support material which possesses sufficient Bronsted acidity to displace at least one of the ligands attached to the said Group VIII metal.

According to a third aspect of our invention we provide a catalyst for the oligomerisation of ethylene comprising the product of reacting a catalyst component as defined above with a Group I to III hydrocarbyl compound.

It is preferred that the ethylene is brought into contact with a slurry of the supported Group VIII metal compound or supported catalyst (i.e. after addition of the Group I to III metal hydrocarbyl) in a hydrocarbon diluent, which may be aliphatic, aromatic or a mixture of such diluents, for example toluene or hexane, under dry oxygen-free conditions. When the ethylene is first contacted with supported Group VIII metal compound only, it will be appreciated that a Group I to III hydrocarbyl compound must be added subsequently. However, it is possible to contact gaseous ethylene directly with the solid supported catalyst, if desired.

The oligomerisation reaction may be carried out at a temperature in the range −40 to +120° C, preferably 0 to 50° C. Reaction pressures up to 50 bars may conveniently be used; but higher pressures may be used if desired.

The oligomeric products may be recovered from the reaction mixture by any convenient technique, but it is preferably accomplished by fractional distillation.

Although, as previously mentioned, our catalysts may be, and are preferably, used in the absence of phosphines, the possibility of the addition of these or other Lewis bases, e.g. pyridine or ethylamine is not precluded.

Our invention will now be illustrated by the following examples.

EXAMPLES 1 AND 2

Preparation of aluminium phosphate

Aluminium phosphate hydrochloride (AlPO$_4$2HCl 2H$_2$O) (62 g) was dissolved in 250 ml distilled water. Ammonia (2-3M) was added dropwise until the pH had risen from about 1.5 to 4, when a further 250 ml of water was added. Addition of ammonia continued until the pH had reached about 8. The gel which formed was filtered, washed twice with distilled water and dried for 4 days at 120° C. The sample was then ground and calcined in nitrogen for 2 hours at 500° C.

Preparation of catalyst (I)

All operations were carried out under dry nitrogen. Calcined aluminium phosphate (2.9 g) was slurried with 40 ml of dry, oxygen-free toluene and 6.8 ml of 0.1M solution of anhydrous nickel acetylacetonate in toluene were added and the slurry stirred for 45 minutes. When allowed to settle, the solid material was yellow and the supernatant liquor colourless. The supernatant liquor was shown to contain acetylacetone by gas/liquid chromatography (GLC). A 2M solution of trimethyl aluminium in toluene (1.4 ml) was then added to the slurry with stirring, the slurry becoming dark brown. The ratio of Al (CH$_3$)$_3$)$_3$/Ni was 4.

EXAMPLE 1

Dry oxygen-free toluene (400 ml) was added to a 1 litre autoclave which had been previously evacuated for at least 1 hour at 140° C. The pressure in the autoclave was brought to just above one atmosphere with dry, oxygen-free ethylene and the temperature adjusted to 65° C. A slurry containing 0.9 g of the catalyst (I) was syringed into the autoclave and the ethylene pressure raised to 35 bars. Samples of gas and liquid were taken at intervals throughout the reaction, the reaction being stopped by venting the ethylene. Final samples were taken just before termination. All samples were analysed by GLC using ethylene and toluene as internal standards for the gas and liquid samples respectively. The butene yield was obtained from the calculated solubility of butene in the ethylene/toluene mixture.

The reaction was found to have yielded

| | |
|---|---|
| Butene-1 | 13.0 g |
| Hexene-1 | 0.16 g |
| Butene-2 | 1.4 g |
| Other Hexenes | 0.14 g |

The selectively to α-olefins was 90% of which >99% was butene and hexene. The activity to α-olefins calculated from the total yield of α-olefins per millimole of Group VIII metal, was 60 g/m mole Ni/hour. Selectivities are expressed as % by weight.

EXAMPLE 2

The procedure of Example 1 was followed with a new batch of catalyst prepared by a similar method to that described above, but using 1.1 g of the catalyst and an oligomerisation reaction temperature of 30° C. After 1 hour, the products comprised:

| | |
|---|---|
| Butene-1 | 41 g |
| Butene-2 | 3.5 g |
| Hexene-1 | 0.4 g |
| Other Hexenes | 0.3 g |

Selectivity to α-olefins = 92%. Activity = 180 g/m mole Ni/hour.

COMPARATIVE EXAMPLE A

The general procedure for the preparation of catalyst (I) was followed but no aluminium phosphate was added. The product catalyst (II), was used according to the oligomerisation procedure in Example 1. The activity was only 0.05 g/m mole Ni/hour and selectivity 70%. Thus, the presence of aluminium phosphate as catalyst support in Examples 1 and 2 had increased both activity and selectivity to 60 -olefins.

COMPARATIVE EXAMPLE B

A catalyst (III) was prepared according to the general preparation of catalyst (I) but the aluminium phosphate was replaced by dried grade B alumina. When tested according to Example 1, it gave an activity of 0.07 g/m mole Ni/hour and selectivity of 91%. Thus, aluminium phosphate, possessing the desired Bronsted acidity, was superior to alumina as a support.

COMPARATIVE EXAMPLE C

A catalyst composition (IV) was prepared by the general procedure used above, using 0.24 m moles of nickel acetylacetonate and 0.95 g of AlPO$_4$ but without the addition of trimethyl aluminium. This catalyst yielded no detectable quantity of butenes when used in the oligomerisation of ethylene.

EXAMPLE 3

Preparation of zirconium phosphate

Zirconyl chloride (96.6 g) was dissolved in 750 ml of distilled water. Orthophosphoric acid (22.6 ml) was diluted with 500 ml of distilled water and added rapidly, with stirring, to the solution of zirconyl chloride. A dense white precipitate formed immediately and the resulting slurry was stirred for a further 20 minutes, at the end of which time the zirconium phosphate was filtered, dried and calcined at 500° C for 2 hours. The zirconium phosphate so produced had a surface area of 170 m$^2$ g$^{-1}$ and a pore volume of 0.74 cc/g.

PREPARATION OF CATALYST AND OLIGOMERISATION PROCEDURE

A supported catalyst was prepared according to the general method described under Examples 1 and 2 except that zirconium phosphate, prepared as described above, was used in place of aluminium phosphate. An oligomerisation was carried out as described in Example 6, below, at 32 bars and 30° C. Activity to α-olefins was 30 g/m mole Ni/hour at a selectivity to α-olefins of 77%.

EXAMPLE 4

Use of PCl$_3$-treated Silica

Fumed silica was vacuum dried at 800° C for 2 hours and then contacted with PCl$_3$ vapour at 300° C for about 15 minutes. The solid product was then exposed to water vapour at 300° C for about 5 minutes, followed by wet air at 800° C for 15 minutes. Finally it was vacuum dried at 500° C. This procedure was then repeated twice. Infra-red spectroscopic (IR) examination of the solid product showed the existence of P-OH groups on silica and chemical analysis indicated the presence of 5% P$_2$O$_5$. The solid product was used in place of aluminium phosphate to prepare an oligomerisation catalyst as described under Examples 1 and 2. When the catalyst was used to oligomerise ethylene at 30° C it gave an activity to α-olefins of >10 g/m mole Ni/hour with a selectivity to α-olefins of 92%.

EXAMPLE 5

The general procedure of Example 1 was followed, except that Al triethyl was substituted for Al trimethyl and the oligomerisation reaction was carried out at 26° C and 32 bars. The activity to α-olefins was 21 g/m mole Ni/hour with a selectivity of 96% to α-olefins.

EXAMPLE 6

Nickel acetylacetonate was supported on aluminium phosphate as described in Example 1, but no aluminium trimethyl was added.

The supported nickel acetylacetonate (0.09 m moles of nickel acetylacetonate on 0.44 g of aluminium phosphate) was then syringed into the autoclave against a stream of ethylene. Trimethylaluminium (1.10 m mole) was then added to the autoclave by syringe, giving an Al/Ni ratio of 12. The temperature was adjusted to 30° C and the ethylene pressure to 35 bars, to cause oligomerisation to take place. The activity to α-olefins was 170 g/m mole Ni/hour with a selectivity of 91% to 60 -olefins. Approximately 97% of the product was butene, 2% hexene by weight and less than 1% higher oligomers.

EXAMPLE 7

The general procedure of Example 6 was followed except that nickel 4 -cyclohexylbutyrate was used instead of nickel acetylacetonate. Ethylene oligomerisation was carried out at 28° C and a pressure of 33 bars. Activity to 60 -olefins was 100 g/m mole Ni/hour with a selectivity of 90% to α- olefins.

EXAMPLES 8–9

The procedure of Example 6 was followed except that the ratio of Group I to III metal to Group VIII metal (i.e. Al/Ni) varied. The results are summarised in Table 1 below.

Table 1

| Example | Mole ratio Aluminium trimethyl /Ni | Pressure (Bars) | Activity g/m mole Ni/hr | Selectivity to α-olefins |
|---------|-----------------------------------|-----------------|-------------------------|--------------------------|
| 8 | 5 | 31 | 110 | 90% |
| 9 | 20 | 35 | 180 | 91% |

EXAMPLE 10

The general procedure of Example 6 was followed except that cobalt (II) acetylacetonate was used instead of nickel. Cobalt (II) acetylacetonate (0.20 m moles) was supported on 0.55 g of aluminium phosphate and 0.80 m moles trimethylaluminium were added as described under Examples 1 and 2. The catalyst so produced was then used to oligomerise ethylene at 26° C and 35 bars. Activity was 60 g/m mole Co/hr with a selectivity to α-olefins of 98%. More than 99% of the product was butene.

EXAMPLE 11

The general procedure of Example 6 was followed except that palladium acetylacetonate was used in place of nickel and the molar ratio of aluminium methyl to Pd was 100.

Activity to α-olefins was 37 g/m mole Pd/hr, with a selectivity to 60 -olefins of 93%.

What we claim is:
1. A process for the oligomerisation of ethylene in which the ethylene is contacted with a catalyst which is the reaction product of a weak field ligand complex of a metal of Group VIII of the Periodic Table and an inorganic oxide support material which contain other elements to impart sufficient Bronsted acidity to said support to displace at least one of the ligands attached to the said Group VIII metal, in the presence of a hydrocarbyl of a metal of Groups I to III of the Periodic Table.
2. A process as claimed in claim 1 in which the weak field ligan complex is a compound of nickel or cobalt.
3. A process as claimed in claim 1 in which the weak field ligand complex is a β-diketone, a β-ketocarboxylic acid ester or a salt of a saturated or unsaturated carboxylic acid.
4. A process as claimed in claim 3 in which the complex is selected from nickel acetyacetonate, nickel 4-cyclohexylbutyrate, cobalt (II) acetylacetonate and palladium acetylacetonate.
5. A process as claimed in claim 1 in which said other element is phosphorus.
6. A process as claimed in claim 5 in which the support material is selected from zirconium phosphate, aluminium phosphate and silica which has been pretreated with phosphorus trichloride.
7. A process as claimed in claim 1 in which the Group I to III metal hydrocarbyl compound is an aluminium trialkyl.

8. A process as claimed in claim 1 in which the molar ratio of Group I to III metal hydrocarbyl compound to Group VIII metal is in the range 20 to 1.

9. An oligomerisation process as claimed in claim 1 in which the reaction temperature is in the range 0 to 50° and the reaction pressure is not more than 50 bars.

10. A mixture of predominantly α-olefin ethylene oligomers whenever prepared by a process as claimed in claim 1.

11. A process as claimed in claim 1, wherein said support is an inorganic oxide, inorganic phosphate, or mixtures thereof.

12. A process according to claim 1, wherein said element is in chemical combination with the oxide of the support material.

* * * * *